United States Patent
Bossi et al.

(10) Patent No.: US 7,478,569 B2
(45) Date of Patent: Jan. 20, 2009

(54) NON-DESTRUCTIVE INSPECTION SYSTEM WITH FLEXIBLE DISPLAY AND ASSOCIATED METHOD

(75) Inventors: Richard H. Bossi, Renton, WA (US); Gary E. Georgeson, Federal Way, WA (US)

(73) Assignee: The Boeing Company, Chicago, IL (US)

( * ) Notice: Subject to any disclaimer, the term of this patent is extended or adjusted under 35 U.S.C. 154(b) by 101 days.

(21) Appl. No.: 11/292,927

(22) Filed: Dec. 2, 2005

(65) Prior Publication Data

US 2007/0125189 A1 Jun. 7, 2007

(51) Int. Cl.
*G01N 29/04* (2006.01)
(52) U.S. Cl. .......................... 73/865.8; 73/625; 73/643
(58) Field of Classification Search ................ 73/865.8, 73/626, 625, 628, 643
See application file for complete search history.

(56) References Cited

U.S. PATENT DOCUMENTS

| | | | |
|---|---|---|---|
| 5,680,863 A | 10/1997 | Hossack et al. | |
| 5,735,282 A | 4/1998 | Hossack | |
| 6,106,463 A * | 8/2000 | Wilk | 600/437 |
| 6,424,597 B1 | 7/2002 | Bolomey et al. | |
| 6,678,403 B1 * | 1/2004 | Wilk | 382/152 |
| 6,746,402 B2 * | 6/2004 | Ustuner | 600/462 |
| 2004/0187184 A1* | 9/2004 | Rubin et al. | 2/69 |
| 2006/0238494 A1* | 10/2006 | Naranyanaswami et al. | 345/156 |
| 2006/0254369 A1* | 11/2006 | Yoon et al. | 73/862.041 |
| 2007/0020445 A1* | 1/2007 | Liu et al. | 428/195.1 |
| 2007/0053498 A1* | 3/2007 | Mandelkern et al. | 378/184 |

OTHER PUBLICATIONS

Flexible Ultrasonic Arrays, *HD Laboratories, Inc., NDT and Electronic Engineers*; 2 pages, available at http://www.hdlabs.com/NDT/FlexibleArrays/flexiblearrays.htm; downloaded Sep. 1, 2005.

* cited by examiner

*Primary Examiner*—Hezron Williams
*Assistant Examiner*—Nashmiya S Fayyaz
(74) *Attorney, Agent, or Firm*—Alston & Bird LLP

(57) ABSTRACT

A system and method for inspecting a structure are provided. The system includes a data system that is capable of providing information indicative of at least a portion of the structure. The system also includes a flexible display that is positioned proximate to the structure and in communication with the data system. The flexible display is capable of displaying an image indicative of at least a portion of the structure based on the information provided by the data system.

19 Claims, 8 Drawing Sheets

NON-DESTRUCTIVE INSPECTION SYSTEM WITH FLEXIBLE DISPLAY AND ASSOCIATED METHOD

BACKGROUND OF THE INVENTION

1) Field of the Invention

Embodiments of the present invention relate to non-destructive inspection and, more particularly, to a non-destructive inspection system utilizing a flexible display and capable of inspecting a structure for defects.

2) Description of Related Art

Non-destructive inspection (NDI) of structures involves thoroughly examining a structure without harming the structure or requiring its significant disassembly. Non-destructive inspection is typically preferred to avoid the schedule, labor, and costs associated with removal of a part for inspection, as well as avoidance of the potential for damaging the structure. Non-destructive inspection is advantageous for many applications in which a thorough inspection of the exterior and/or interior of a structure is required. For example, non-destructive inspection is commonly used in the aircraft industry to inspect aircraft structures for any type of internal or external damage to or defects (flaws) in the structure. Inspection may be performed during manufacturing or after the completed structure has been put into service, including field testing, to validate the integrity and fitness of the structure. In the field, access to interior surfaces of the structure is often restricted, requiring disassembly of the structure, introducing additional time and labor.

Nondestructive testing is routinely performed on metallic and composite structures including panels, fastened assemblies, composite laminates, composite or metallic sandwich structures and bonded assemblies. These structures, in applications such as aerospace, require that devices and processes are available to ensure structural integrity, production quality, and life-cycle support for safe and reliable use. As such, it is frequently desirable to inspect structures to identify any defects, such as cracks, corrosion, discontinuities, voids, porosity, disbands or delaminations which could adversely affect the performance of the structure at the time of manufacture and at periodic inspections during the life of the structure. Inspections are also required when internal damage is suspected due to unintended occurrences to the structure. Many structures have complex shapes that complicate the inspection and must be compensated for by the inspection method.

Various types of sensors may be used to perform non-destructive inspection. One or more sensors may move over the portion of the structure to be examined, and receive data regarding the structure. For example, a pulse-echo (PE) sensor may be used to obtain ultrasonic data, such as for thickness gauging or corrosion detection, detection of laminar defects and porosity, and/or crack detection in the structure. Resonance or mechanical impedance sensors are typically used to provide indications of delamination or debonding, such as in adhesive bondlines of the structure. Eddy current sensors are used to detect cracks and corrosion in metallic structures. Data mapping is commonly performed to provide a plan view image of the condition of the part or structure under inspection. Data acquired by sensors is typically processed and then presented to a user via a display as an image of the inspected structure. To increase the rate at which the inspection of a structure is conducted, a scanning system may include arrays of inspection sensors, i.e., arrays of transmitters and/or detectors.

Non-destructive inspection may be performed manually by technicians who typically move an appropriate sensor over the structure. Manual scanning requires a trained technician to move the sensor over all portions of the structure needing inspection. Manual scanning typically involves the technician repeatedly moving a sensor side-to-side in one direction while simultaneously indexing the sensor in another direction. In addition, because sensors typically do not associate location information with the acquired data, the same technician who is manually scanning the structure must also watch the sensor display while scanning the structure to determine where the defects, if any, are located in the structure. The quality of the inspection, therefore, depends in large part upon the technician's performance, not only regarding the motion of the sensor, but also the attentiveness of the technician in interpreting the displayed data. Thus, manual scanning of structures is time-consuming, labor-intensive, and prone to human error.

Semi-automated inspection systems have also been developed. For example, the Mobile Automated Scanner (MAUS®) system is a mobile scanning system that generally employs a fixed frame and one or more automated scanning heads typically adapted for ultrasonic inspection. A MAUS system is typically used with pulse-echo or resonance sensors. The fixed frame may be attached to a surface of a structure to be inspected by vacuum suction cups, magnets, or like affixation methods. MAUS systems may be used with a portable head that is manually moved over the surface of a structure by a technician, while the sensors are moved side to side within the head. Alternatively, a linear array of sensors can be scanned in one direction by the MAUS to create a 2D image of the structure.

When inspecting a structure, a display is typically needed in order to view images of the structure being inspected. For example, on-site inspection may require a computer or laptop having a screen for viewing displayed images and processing data associated with the displayed images. However, the image display information must be accurately transferred to registered locations in the structure.

It would therefore be advantageous to provide a non-destructive inspection system that is capable of accurately transferring a displayed image onto a structure. In addition, it would be advantageous to provide an inspection system that is portable, lightweight and capable of inspecting structures effectively and efficiently with the results displayed proximate to the inspection zone. Furthermore, it would be advantageous to provide a non-destructive inspection system that is economical to manufacture and use.

BRIEF SUMMARY OF THE INVENTION

Embodiments of the invention address the above needs and achieve other advantages by providing an inspection system that utilizes a lightweight flexible display for displaying images of a portion of a structure being inspected. The inspection system utilizes one or more sensors to acquire data indicative of a structure and communicates the data to a data acquisition system for processing. The data acquisition system generates information and communicates that information to the flexible display to display an image representing the inspected area of the structure. The flexible display is pliable and capable of conforming to the surface of the structure such that the display may be positioned at least indirectly in contact with the structure. As a result, the locations of specific areas shown on the display, such as flaws, may be readily transferred to the structure for repair or replacement of the structure.

In one embodiment of the present invention, a system for inspecting a structure is provided. The system includes a data system capable of providing information indicative of at least a portion of the structure. The system also includes a flexible display that is positioned proximate to the structure and in communication with the data system. The flexible display is capable of displaying an image indicative of at least a portion of the structure based on the information provided by the data system.

In aspects of the system, the system further includes a sensor assembly having a flexible sheet of material and at least one sensor or an array of sensors attached thereto. The flexible sheet of material may be a polymeric material, such as a polyvinylidene fluoride material, and at least a portion of the sensor assembly may be configured to be positioned adjacent to the structure and/or flexible display. When positioned adjacent to the sensor assembly, the flexible display is capable of displaying the image while being positioned thereon. A surface of the structure located adjacent to the sensor assembly may be non-planar such that the sensor assembly and/or flexible display may conform to the non-planar surface.

According to additional modifications of the system of the present invention, the system includes at least one sensor (e.g., an ultrasonic or an eddy current sensor) positioned proximate to the structure. The flexible display could be positioned adjacent to the sensor(s). The data system may be in communication with the sensor and is capable of generating information indicative of a defect in the structure based on information acquired by the sensor. The flexible display may be capable of displaying an image indicative of the defect. Furthermore, the flexible display may be capable of displaying an ultrasonic A-scan, B-scan, or C-scan, an ultrasonic resonance image, an eddy current image, or an impedance plane signal image of the portion of the structure.

Another aspect of the present invention also provides a method for inspecting a structure. The method includes positioning a flexible display proximate to the structure, and providing information indicative of at least a portion of the structure. The method further includes displaying an image indicative of at least a portion of the structure with the flexible display based on the provided information.

In various aspects of the method, the positioning step further includes positioning at least one sensor proximate to the structure. The positioning step may include positioning at least a portion of a sensor assembly carrying the sensor(s) adjacent to the structure and/or flexible display. The displaying step could include displaying the image while the flexible display is positioned adjacent to the sensor assembly. Moreover, the positioning step may include positioning the flexible display adjacent to the sensor(s). The providing step may include generating information indicative of a defect within the structure based on the data acquired by the sensor(s), and the displaying step may further include displaying an image indicative of the defect. The acquiring step may include acquiring data indicative of at least a portion of the structure through the flexible display. In addition, the method could include updating the displayed image while the sensor acquires data indicative of the structure. The displaying step could include displaying an A-scan, a B-scan, or a C-scan image of the portion of the structure.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Figure 1A:
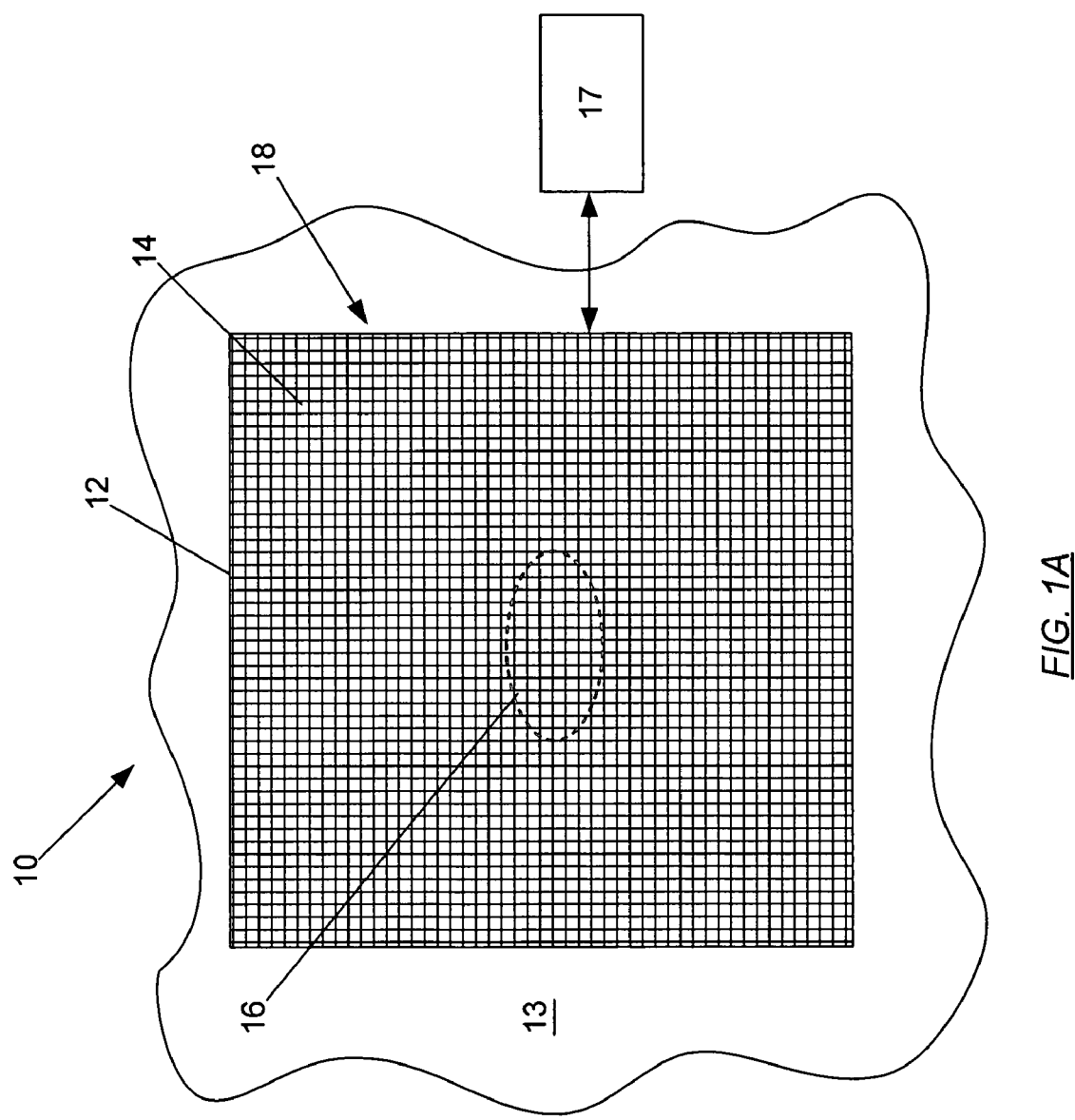
FIGS. 1A-1B are plan views of an inspection system according to one embodiment of the present invention.
Figure 1B:
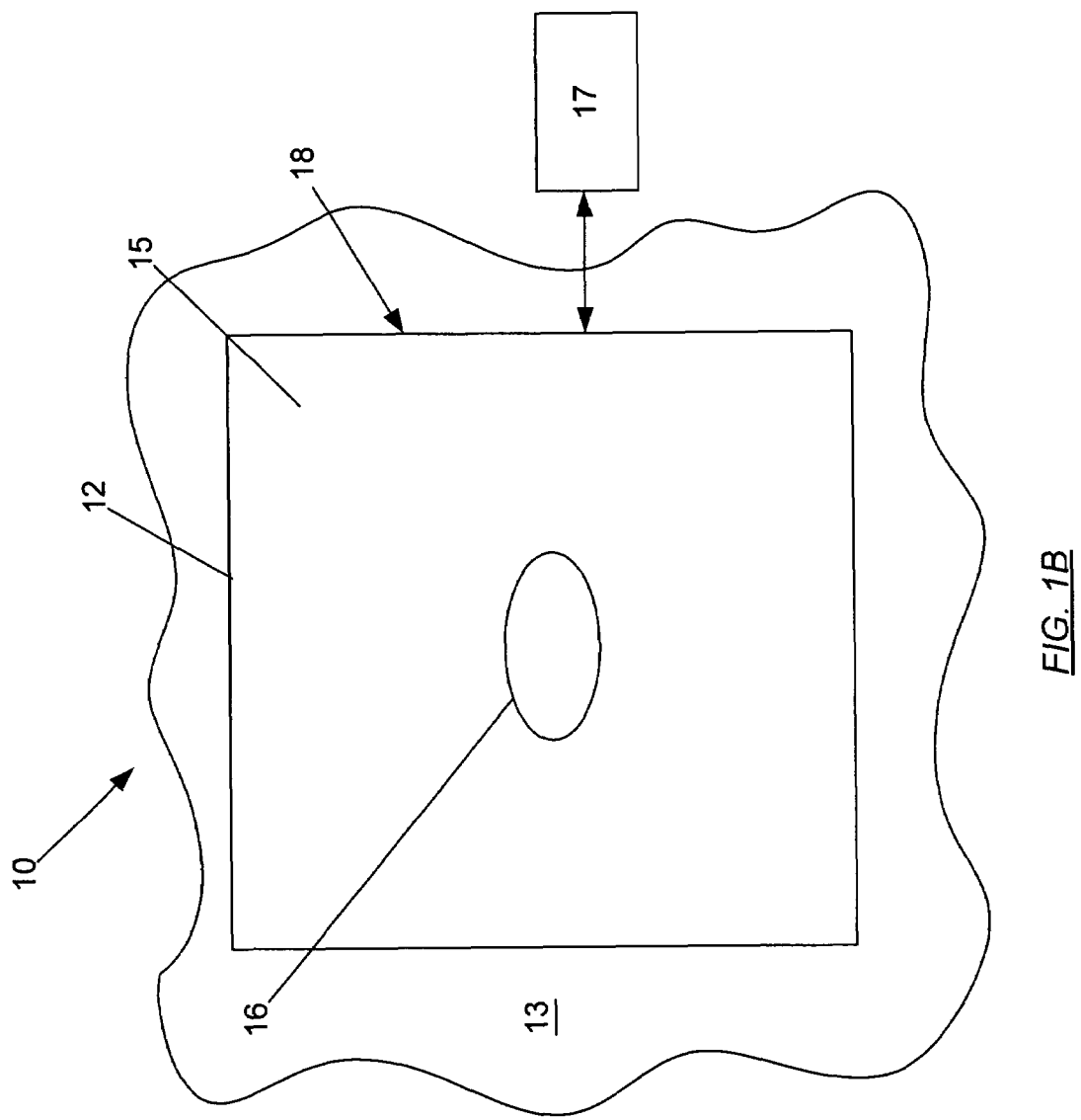

Referring now to the drawings and, in particular to FIGS. 1A-1B, there is shown an inspection system 10. The inspection system 10 includes a sensor assembly 18 having a plurality of non-destructive sensors 14 arranged thereon. The sensors 14 are capable of detecting a flaw 16 in a structure 13 and are in communication with a data acquisition system 17. A flexible display 15 may be positioned adjacent to the sensor assembly 18 and is capable of generating various images of a portion of the structure based on information generated by the data acquisition system 17.

The inspection system 10 could be used to inspect any number of structures 13 in a variety of industries where detection of flaws or defects in the structure is required, such as in the aircraft, automotive, marine, or construction industries. The sensors are capable of detecting any number of flaws or defects within or along the surface of the structure, such as impact damage (e.g., delaminations and matrix cracking), disbonds (e.g., airframe/reinforcing members or honeycomb composites), discontinuities, voids, or porosity, which could adversely affect the performance of the structure. In addition, the sensors 14 could be utilized for various other purposes, such as for identifying ply count or thickness.

The term "structure" is not meant to be limiting, as the inspection system 10 could be used to inspect any number of parts or structures of different shapes and sizes, such as machined forgings, castings, pipes, or composite panels or parts. The inspection could be performed on newly manufactured structures or existing structures that are being inspected for preventative maintenance purposes. In addition, the structure could include various components. For instance, the structure could include a substructure for providing additional support to the structure. Further, the structure could be any number of materials. For example, the structure could be a metallic material, such as aluminum, or a composite material, such as graphite-epoxy. Moreover, the structure could be an aircraft, such as the Boeing Dreamliner 787, where a substantial portion of the aircraft structure is a composite material (e.g., the fuselage and wings).

The sensor assembly 18 includes a flexible sheet of material 12. The flexible sheet of material 12 is typically a nonconductive sheet that is flexible and pliable. For example, the sheet of material 12 could be a thin polymeric material, such as polyvinylidene fluoride ("PVDF") or micro sensors arranged on a flexible sheet, although various passive materials may be employed in additional aspects of the present invention. Providing a flexible sheet of material 12 allows the sheet to be manipulated to conform to a variety of surface contours for inspection, as well as maintain intimate contact with the underlying structure. The sheet of material 12 could be various dimensions to accommodate different sizes of structures for inspection (e.g., 8"×8" or 2"×8"). For example, the sheet of material 12 could be smaller than the structure under inspection and incrementally moved along the structure for inspecting portions of the structure.

Each of the non-destructive sensors 14 utilized with the sensor assembly 18 could be any suitable sensor or transducer capable of transmitting and receiving signals 22, as well as communicating with the data acquisition system 17. Each sensor 14 is typically a non-destructive sensor, such that the sensor is capable of inspecting a structure without harming the structure 13 or requiring disassembly of the structure. In one embodiment of the inspection system 10, each sensor 14 is an ultrasonic sensor, such as used in a pulse-echo mode. Thus, the pulse-echo sensor would transmit and receive ultrasonic signals 22 generally perpendicular to the surface of the structure 13. However, various other sensors 14 may be employed with the inspection system 10 of the present invention, such as pitch-catch, eddy current, through-transmission (e.g., a sensor(s) could be placed on the opposite surface of the structure 13 and transmit a signal through the structure that is received by the sensors 14, or vice versa), shear-wave, resonance, or mechanical impedance sensors. For instance, pitch-catch sensors could be arranged on the sheet of material 12 such that one sensor could transmit an ultrasonic signal into the structure and be picked up by a receiving sensor.

The sensors 14 may be arranged on the flexible sheet of material 12 in a variety of configurations. For example, FIG. 1A illustrates that the sensors 14 are arranged linearly in rows and columns to define an array (the flexible display 15 has been removed for purposes of depicting the sensor array). For instance, there could be an array of 100×100 sensors 14 on the sheet of material 12. However, it is understood that the sensors 14 may be arranged in any number of configurations on the sheet of material 12 and may be spaced apart from one another. For instance, the sensors 14 could be arranged about the perimeter of the sheet of material 12 (e.g., pitch-catch sensors). As the number of sensors 14 increases, or the distance between the sensors decreases, the smaller the flaw that may be detected. Therefore, the number and/or arrangement of the sensors 14 may be varied depending on the size of the flaw to be detected and to achieve a particular resolution of the inspection image.

Figure 2:
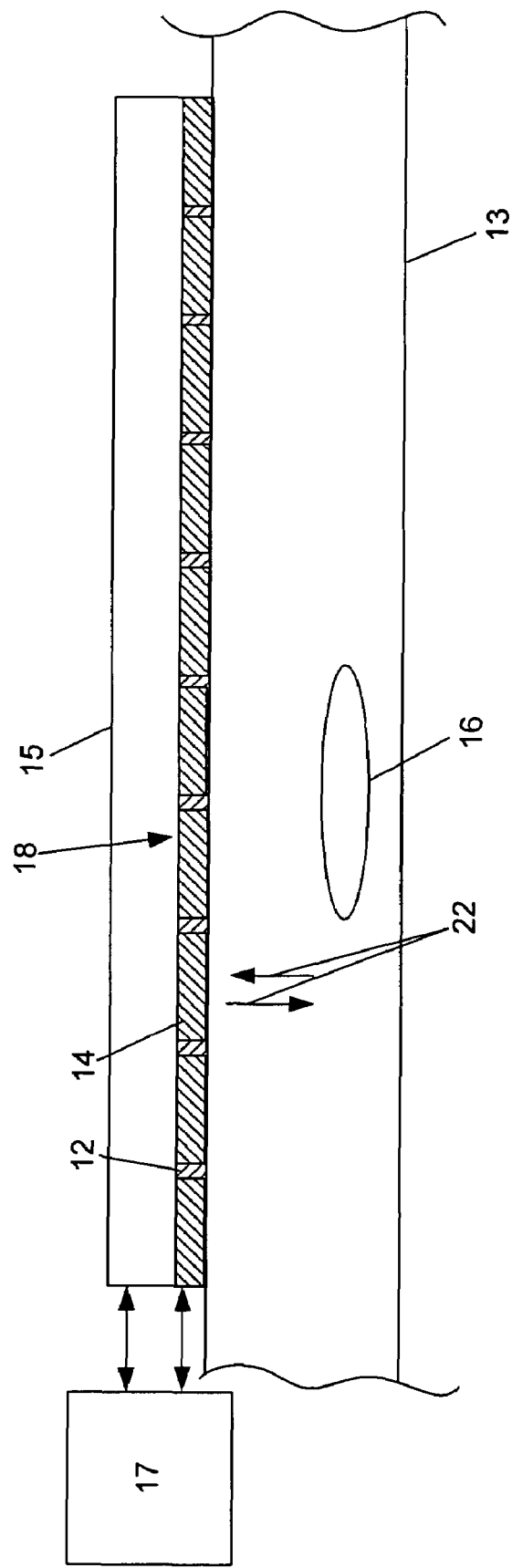
FIG. 2 is a cross-sectional view of an inspection system according to another embodiment of the present invention.

The sensors 14 may be integrated with the flexible sheet of material 12 in a sensor assembly 18. Thus, the sensors 14 may be attached, or otherwise secured, to the sheet of material 12 such that each sensor is proximate to the structure 13 when the sensor assembly 18 is positioned on the structure, as shown in FIG. 2. It is understood that various techniques could be utilized to integrate the sensors 14 with the sheet of material 12, such as individually attaching sensors to the sheet of material or utilizing transducers that are integrated in the sheet of material. Thus, the individual sensors 14 could be attached to the sheet of material or be flexibly attached to one another. Alternatively, transducers or electrodes could be integrated into the sheet of material 12 and send/receive signals 22 so as to function like individual sensors 14.

The data acquisition system 17 typically includes a processor or similar computing device operating under the control of software so that data acquired by the sensors 14 may be analyzed. The processor could be embodied by a computer such as a desktop, laptop, tablet computer, or portable processing device capable of processing the data generated by the sensors 14. Furthermore, the data acquisition system 17 typically includes a pulser/receiver card, or similar device, so that the sensors 14 are capable of transmitting signals 22 within and receiving signals from the structure 13, such as ultrasonic stress waves. Thus, each sensor 14 is typically in communication with the data acquisition system 17, either directly or via a network, to process the data accumulated by the sensors. In many cases, communication cable(s) transmit data between the sensors 14, the data acquisition system 17, and flexible display 15. In other embodiments, the data may be transmitted between the sensors 14, data acquisition system 17, and flexible display 15 via wireless communications (e.g., via Bluetooth® technology). The sensors 14 may be directly connected to the data processing system 17, or indirectly connected, such as via a network. In further embodiments of the present invention the data acquisition system 17 may be located proximate to the sensors 14, such that remote connections between the sensor and data acquisition system are not necessary.

The flexible display 15 is typically positioned adjacent to the sensor assembly 18, as depicted in FIG. 2, but may, in other embodiments, be spaced somewhat therefrom. Because the flexible display 15, like the sensor assembly 18, is flexible or pliable, the flexible display is also capable of conforming to a variety of surface contours of the structure 13. For example, the flexible display 15 could be a flexible polymer substrate, a thin-film transistor liquid crystal display ("TFT-LCD"), or an organic thin-film transistor ("OTFT"), as opposed to a rigid glass display. In addition, the flexible display 15 is typically thin so that the display is not only lightweight and portable, but is also capable of conforming to a variety of surfaces. The flexible display 15 may extend to the outer perimeter of the sensor assembly 18 so that the flexible display is capable of displaying images resulting from data acquired by each of the sensors 14 and, in particular, in a one-to-one actual size format. However, the flexible display 15 could be various sizes and configurations for different inspection applications and structures 13. For example, the sensor assembly 18 could cover a much larger surface area than the flexible display 15, and the flexible display could be moved to various locations on the sensor assembly and display an image at each location.

The flexible display 15 is capable of displaying an image indicative of the structure 13, including, for example, at least those flaws detected within the structure, while the flexible display is positioned on the sensor assembly 18. Thus, technicians are capable of readily identifying the location and characteristics of the flaw, defects, or the like without having to refer to a remotely located display, such as a computer screen, and then attempt to transfer the location of the damaged areas from the remotely located display to the structure 13. As a result, technicians may repair/replace the damaged area(s) on the structure 13 or mark the damaged area(s) with a marking device, such as a pen or paint. For instance, the vacuum applied to the sensor assembly 18 may be released so that the sensor assembly may be partially or completely peeled away from the structure 13, and the technician may mark the location of the damaged area(s) accordingly. Consequently, the technician may immediately repair or replace the damaged area(s).

The data acquisition system 17 generates information indicative of the structure 13, including, for example, at least those flaws detected within the structure, based on data acquired by the sensors 14 and provides the flexible display 15 with the information to display an image, such as an ultrasonic A-scan, B-scan, or C-scan, an ultrasonic resonance image, an eddy current image, or an impedance plane signal. The data acquisition system 17 is capable of generating information indicative of a flaw and may also allow a user to store and edit previously created images. Therefore, a permanent record of the images may be kept for future use or record keeping. However, it is understood that in addition to displaying images with the flexible display 15, the data acquisition system 17 could mathematically collect and analyze data that a technician could use to characterize a flaw based on the data.

Although the inspection system 10 disclosed herein has been described as using a sensor assembly 18, flexible display 15, and data acquisition system 17 concurrently, it is understood that the flexible display could be used to display images at various times. For example, pre-stored data that has been acquired by the sensors 14 and processed by the data acquisition system 17 may be stored. The data acquisition system 17, or other data system, could be employed to transmit the stored data to the flexible display 15 at a later time while the flexible display is positioned on or near the structure 13. Thus, the flexible display 15 may be moved to various positions on or near the structure 13 to display respective images corresponding to data acquired at those positions with the sensors 14. The images may be displayed for locating defects and repairing or replacing the structure 13, as described above, and the data stored in the data acquisition system 17 may include location information for ensuring that the location of the displayed image corresponds to the location where data was acquired.

Figure 3:
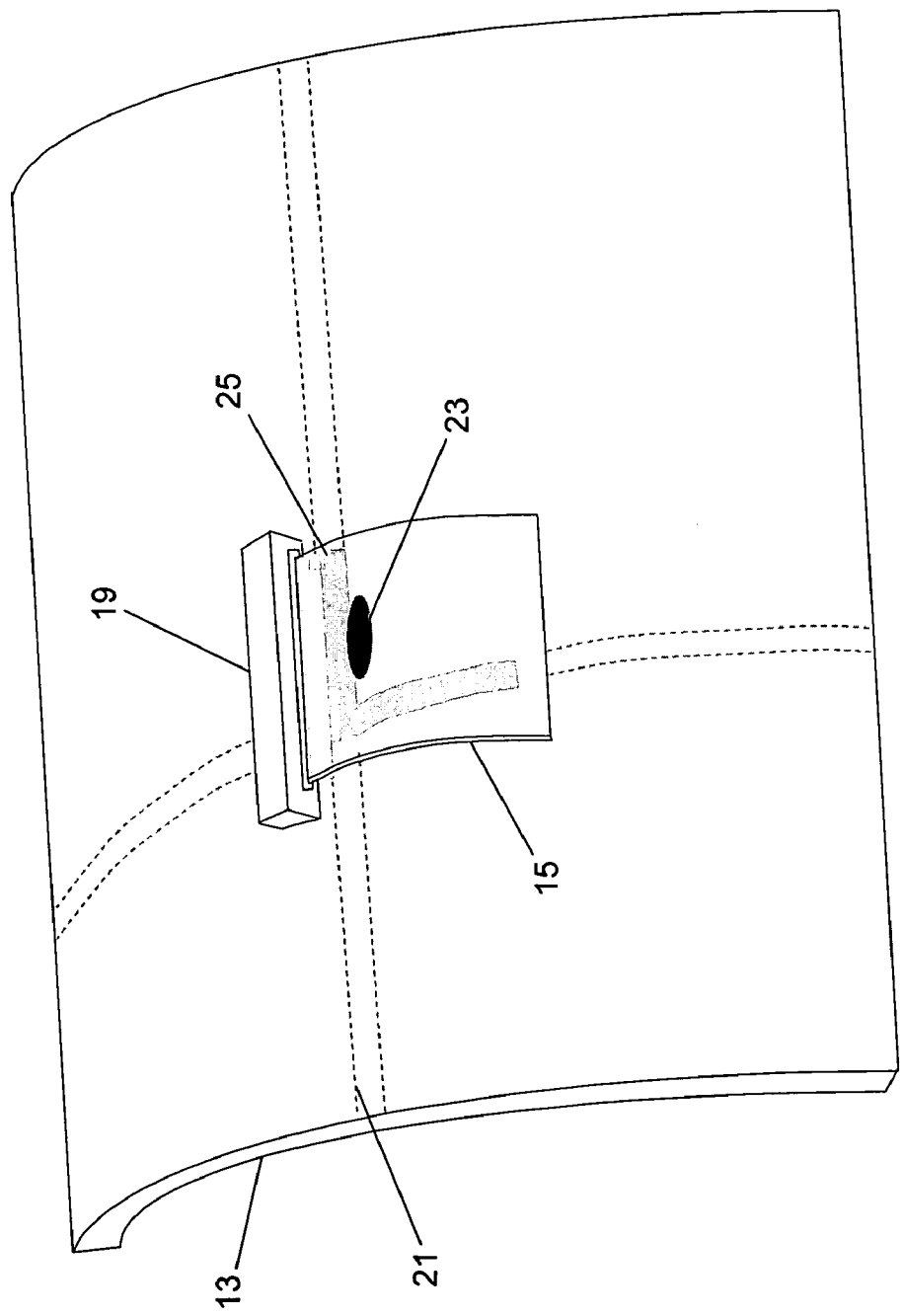
FIG. 3 is a perspective view of an inspection system according to an additional embodiment of the present invention.

FIG. 3 illustrates another embodiment of the present invention where the inspection system includes a suction mount 19. The suction mount 19 enables the flexible display 15 to be secured to the structure 13 during inspection of the structure. In addition, the suction mount 19 may also be configured to allow the flexible display 15 to scroll in and out of the suction mount. The structure 13 shown in FIG. 3 also includes a substructure 21. The flexible display 15 is shown as displaying a flaw image 23 and a structure image 25 that may include a portion of the substructure 21. The structure image 25 may be displayed at the same time that the flaw image 23 is displayed, as shown in FIG. 3.

Figure 4A:
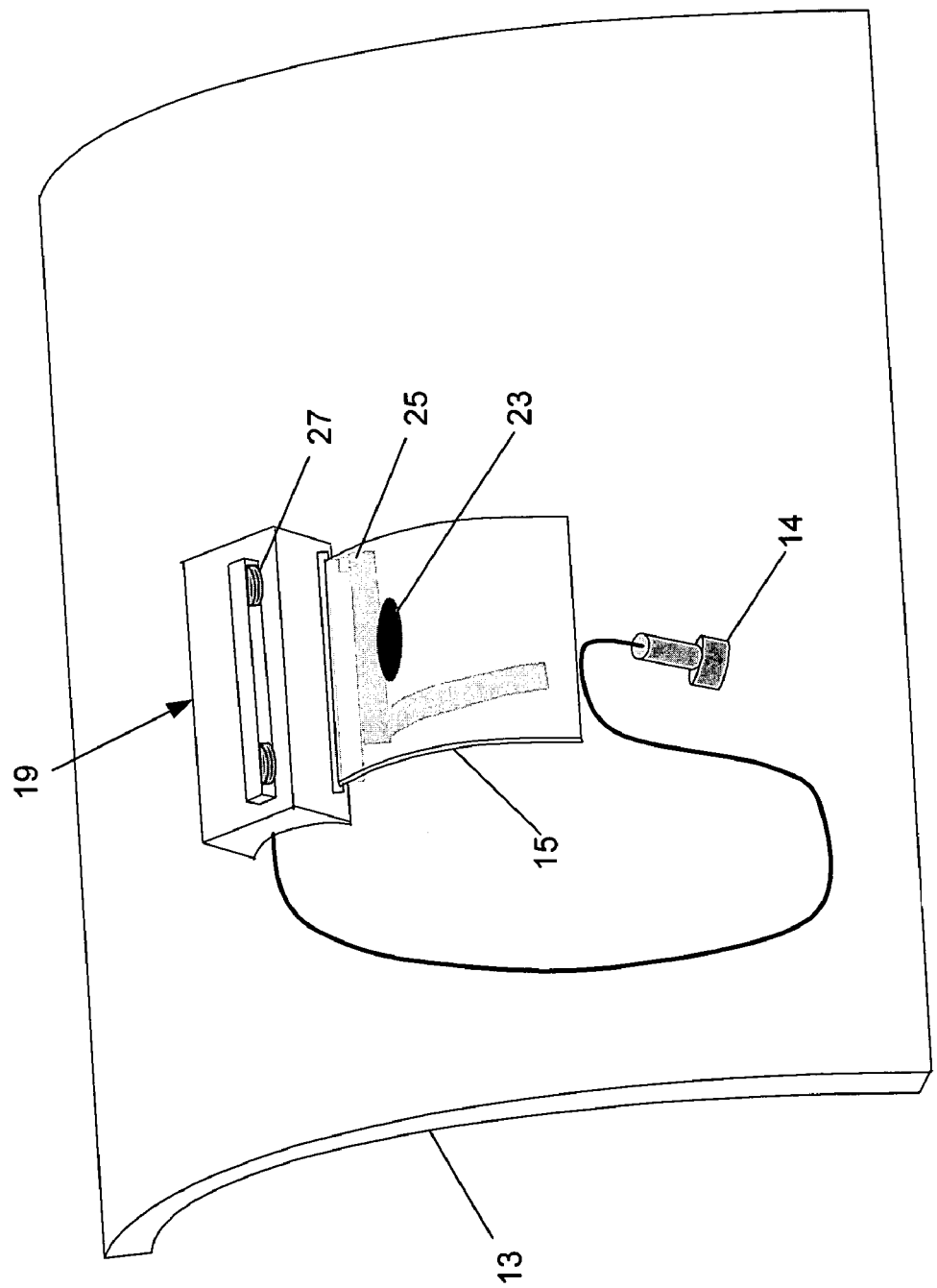
FIGS. 4A-4B are perspective views of an inspection system according to another embodiment of the present invention.
Figure 4B:
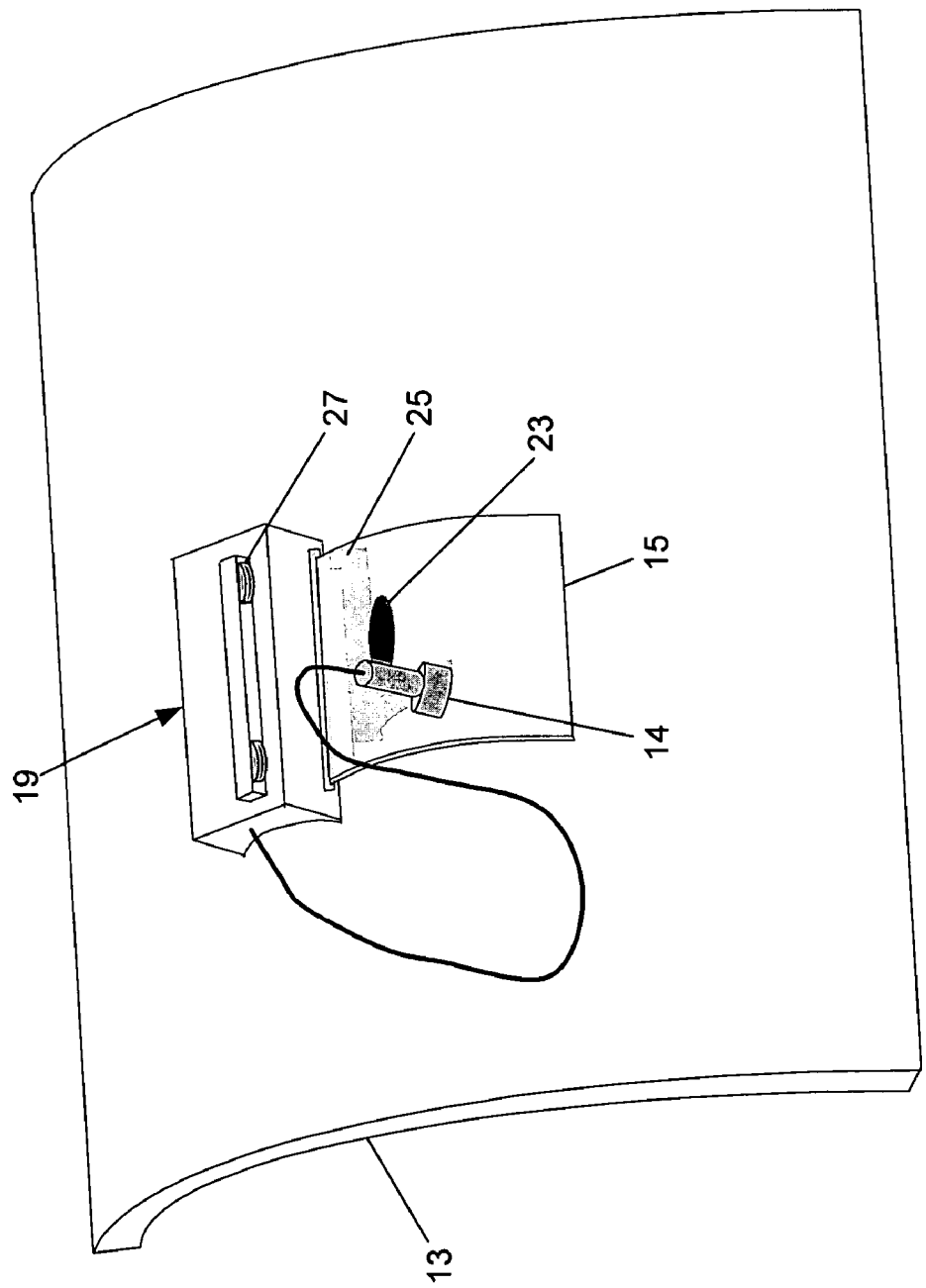

Another embodiment of the present invention is illustrated in FIGS. 4A and 4B. In particular, FIG. 4A illustrates a sensor 14 that is in communication with the suction mount 19. Thus, the suction mount 19 could include a data acquisition system for analyzing the data acquired by the sensor 14. The sensor 14 shown in FIGS. 4A and 4B is a hand-scan transducer that is capable of acquiring data indicative of the structure 13 through the flexible display 15. Thus, the sensor 14 can be moved along the flexible display 15 and acquire data indicative of the structure 13 located below the flexible display.

Furthermore, the suction mount 19 includes a wireless transducer position encoder system 27 that is capable of determining the position of the sensor 14 and/or flexible display 15. Thus, as shown in FIG. 4B, as the sensor 14 is moved over the flexible display 15, the encoder system 27 is capable of providing location information such that data acquired by the sensors may be correlated with the location information. As such, the suction mount 19 may include a data acquisition system that generates information indicative of the structure 13 and communicates the generated information to the flexible display 15 to display, for example, a flaw image 23 and a structure image 25.

Figure 5:
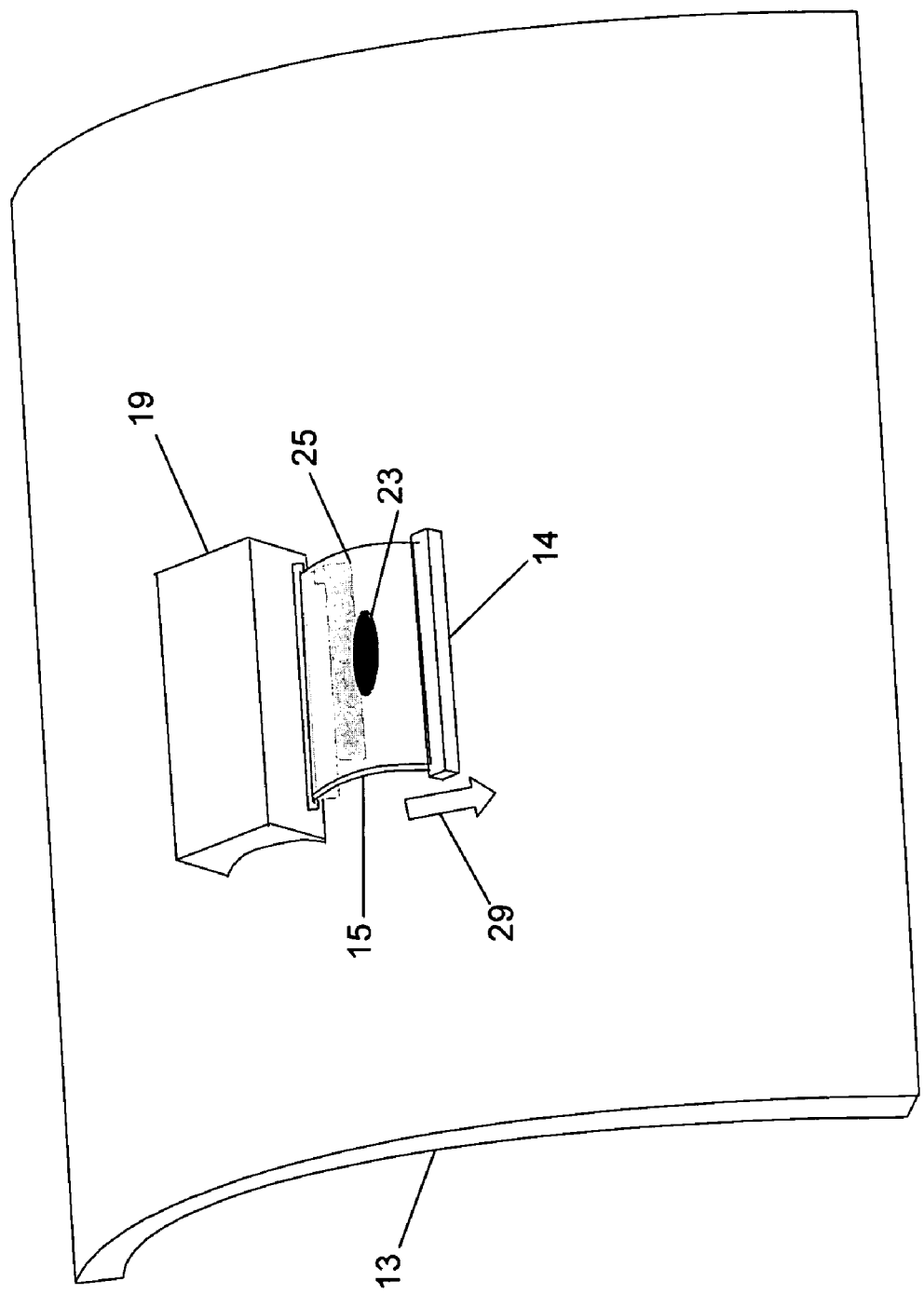
FIG. 5 is a perspective view of an inspection system according to another embodiment of the present invention.

FIG. 5 illustrates another embodiment of the present invention where the flexible display 15 is capable of scrolling into and out of the suction mount 19. As shown in FIG. 5, the arrow 29 shows that the flexible display 15 may scroll outwardly from the suction mount 19. Moreover, a sensor 14 is attached to an opposite end of the flexible display 15. In particular, the sensor 14 comprises a linear sensor array that is capable of acquiring data indicative of the structure 13. The linear sensor array is approximately the width of the flexible display 15. The linear sensor array could acquire data as the flexible display 15 is scrolled out of the suction mount 19. Thus, the location of the linear sensor array could be determined using, for example, an encoder system, and correlated with the data acquired by the linear sensor array to display a flaw image 23 and/or structure image 25 on the flexible display 15. In addition, the images depicted on the flexible display 15 could be updated as the sensor 14 is moved along the structure 13.

Figure 6:
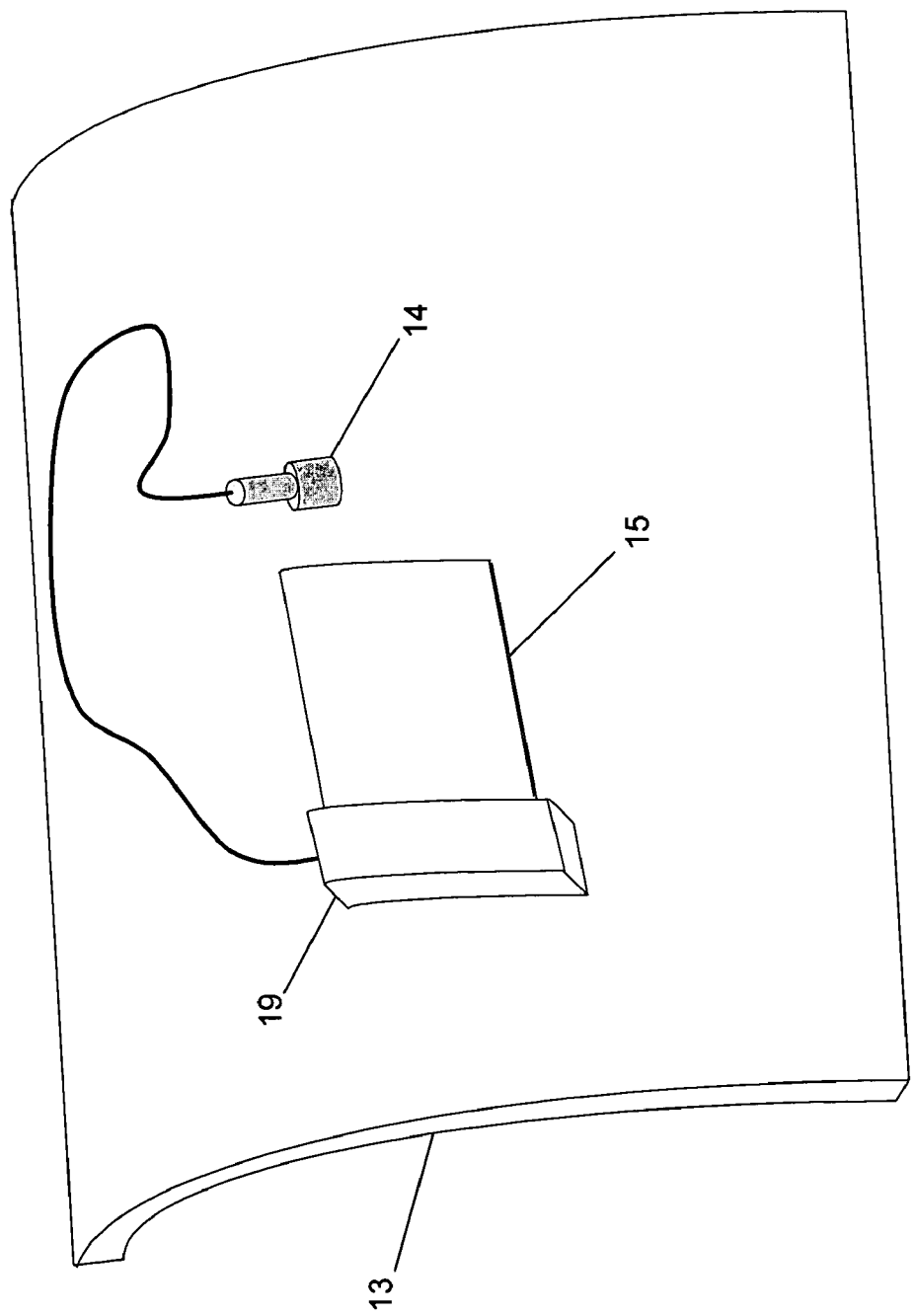
FIG. 6 is a perspective view of an inspection system according to additional embodiment of the present invention.

It is understood that there may be various modifications to the embodiments shown in FIGS. 3-5 in additional aspects of the present invention. For example, although FIGS. 3-5 show that the flexible display 15 extends in a generally vertical direction, the flexible display could be oriented at various orientations and positions. For example, FIG. 6 illustrates that the flexible display may be secured to the structure 13 such that the flexible display 15 extends generally horizontal. The flexible display 15 is capable of scrolling into and out of the suction mount 19, although the flexible display could be attached to the suction mount and not scroll. In addition, although a hand scan transducer and linear sensor array are shown, it is understood that any number and type of sensors 14 may be utilized to acquire data indicative of the structure 13, as described above. Moreover, although a suction mount 19 is shown as securing the flexible display 15 to the structure 13, various techniques could be utilized to secure to the flexible display to the structure, as also discussed above. Furthermore, the suction mount 19 could include a data acquisition system for processing the data from the sensor 14 and/or encoder system 27 as described above or, alternatively, a separate data acquisition system may communicate with the sensor and/or encoder system and generate information for displaying on the flexible display 15. It is also understood that although a wireless transducer encoder system 27 is described above, the inspection system could use similar techniques to determine the position of the sensor(s) 14 and/or flexible display 15. For example, manual scanning arms with position encoders or scanning track systems could be used.

Thus, embodiments of the present invention provide several advantages. For example, the sensor assembly 18 and flexible display 15 allow the inspection system 10 to conform to a variety of surface contours such that the inspection system is suitable for field-level inspections of any number of structures 13. In addition, the inspection system 10 is lightweight, portable, and adaptable to a variety of structures, including aircraft. Because the flexible display 15 is positioned directly on the structure 13 and may display an image while positioned thereon, the potential for error in transferring the location of the flaw onto the structure is reduced.

The inspection system 10 may also be set up quickly and display images on the flexible display 15 in a relatively short period of time after set up. The inspection system 10 also provides quantitative image-based data that conventional hand-held flaw detector ultrasonic testing cannot provide.

Many modifications and other embodiments of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A system for inspecting a structure comprising:
 a sensor assembly comprising a flexible sheet of material and at least one sensor attached thereto;
 a data system in communication with the sensor assembly and configured to provide information indicative of a defect in the structure, wherein the information comprises information indicative of at least one of a crack, corrosion, a discontinuity, a void, porosity, a disbond, or delamination;
 a flexible display positioned proximate to the structure and in communication with the data system such that the flexible display is configured to display an image indicative of the defect in the structure based on the information provided by the data system, wherein the flexible display is configured to display the image while being positioned adjacent to the sensor assembly; and
 a suction mount configured to be coupled to the structure, wherein the flexible display is configured to scroll in and out of the suction mount.

2. The system according to claim 1, wherein a surface of the structure is non-planar and the sensor assembly is configured to conform to the non-planar surface.

3. The system according to claim 2, wherein the sensor assembly further comprises an array of sensors attached to the flexible sheet of material.

4. The system according to claim 2, wherein the flexible sheet of material comprises a polyvinylidene fluoride material.

5. The system according to claim 2, wherein at least a portion of the sensor assembly is configured to be positioned adjacent to at least one of the structure and flexible display.

6. The system according to claim 5, wherein the flexible display is also configured to conform to the non-planar surface.

7. The system according to claim 1, wherein the at least one sensor comprises an ultrasonic sensor.

8. The system according to claim 1, wherein the data system is configured to generate information indicative of a defect in the structure based on information acquired by the at least one sensor.

9. The system according to claim 1, wherein the flexible display is configured to display an ultrasonic A-scan, B-scan, or C-scan, an ultrasonic resonance image, an eddy current image, or an impedance plane signal of the portion of the structure.

10. The system according to claim 1, wherein the at least one sensor comprises an eddy current sensor.

11. The system according to claim 1, wherein the suction mount comprises an encoder system configured to provide a location of the at least one sensor and/or the flexible display.

12. A method for inspecting a structure comprising:
 positioning a sensor assembly comprising a flexible sheet of material and at least one sensor attached thereto proximate to the structure;
 coupling a flexible display to the structure with a suction mount;
 scrolling the flexible display in or out of the suction mount;
 positioning the flexible display adjacent to the sensor assembly;
 providing information indicative of a defect in the structure based upon information from the at least one sensor, wherein the structure is a manufactured metallic or composite material and the information comprises information indicative of at least one of a crack, corrosion, a discontinuity, a void, porosity, a disbond, or delamination; and
 displaying an image indicative of the defect in the structure with the flexible display based on the provided information such that the image is capable of being viewed while the flexible display is positioned adjacent to the sensor assembly.

13. The method according to claim 12, wherein positioning the sensor assembly comprises positioning the sensor assembly on a non-planar surface of the structure such that sensor assembly conforms to the non-planar surface.

14. The method according to claim 12, wherein positioning the sensor assembly comprises positioning at least a portion of the sensor assembly adjacent to the structure.

15. The method according to claim 12, further comprising acquiring data indicative of at least a portion of the structure from the at least one sensor.

16. The method according to claim 15, wherein acquiring comprises acquiring data indicative of at least a portion of the structure through the flexible display.

17. The method according to claim 15, wherein providing comprises generating information indicative of a defect within the structure based on the data acquired by the at least one sensor.

18. The method according to claim 12, further comprising updating the displayed image while the at least one sensor acquires data indicative of the structure.

19. The method according to claim 12, wherein displaying comprises displaying an ultrasonic A-scan, B-scan, or C-scan image, an ultrasonic resonance image, an eddy current image, or an impedance plane signal of the portion of the structure.

* * * * *